(12) United States Patent
Bevinakatti

(10) Patent No.: US 10,335,359 B2
(45) Date of Patent: *Jul. 2, 2019

(54) HAIR FIXATIVES INCLUDING CELLULOSE ESTER BASED POLYGLUCOSE POLYMERS

(71) Applicant: Akzo Nobel Chemicals International B.V., Arnhem (NL)

(72) Inventor: Hanamanthsa Bevinakatti, Somerset, NJ (US)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 365 days.

This patent is subject to a terminal disclaimer.

(21) Appl. No.: 15/100,878

(22) PCT Filed: Dec. 17, 2014

(86) PCT No.: PCT/EP2014/078228
§ 371 (c)(1),
(2) Date: Jun. 1, 2016

(87) PCT Pub. No.: WO2015/091651
PCT Pub. Date: Jun. 25, 2015

(65) Prior Publication Data
US 2016/0303022 A1  Oct. 20, 2016

Related U.S. Application Data

(60) Provisional application No. 61/919,087, filed on Dec. 20, 2013.

(30) Foreign Application Priority Data

Feb. 14, 2014 (EP) .................................. 14155146

(51) Int. Cl.
*A61Q 5/04* (2006.01)
*A61K 8/73* (2006.01)
*A61Q 5/06* (2006.01)
*A61K 8/85* (2006.01)
*A61K 8/04* (2006.01)
*A61K 8/34* (2006.01)

(52) U.S. Cl.
CPC .............. *A61K 8/731* (2013.01); *A61K 8/046* (2013.01); *A61K 8/34* (2013.01); *A61K 8/85* (2013.01); *A61Q 5/06* (2013.01)

(58) Field of Classification Search
None
See application file for complete search history.

(56) References Cited

U.S. PATENT DOCUMENTS

| 4,134,809 A | 1/1979 | Pacifici et al. |
| 2002/0197225 A1 | 12/2002 | Giroud et al. |
| 2003/0147829 A1 | 8/2003 | Oldfield et al. |

FOREIGN PATENT DOCUMENTS

| DE | 10101382 A1 | 8/2002 |
| JP | 2002-265323 A | 9/2002 |
| WO | 99/59532 A1 | 11/1999 |
| WO | 2009/010842 A2 | 1/2009 |

OTHER PUBLICATIONS

European Search Report for EP 14155146.5, dated May 20, 2014.
International Search Report and Written Opinion for PCT/EP2014/078228, dated May 18, 2015.

*Primary Examiner* — Susan T Tran
(74) *Attorney, Agent, or Firm* — Sandra B. Weiss

(57) ABSTRACT

A hair fixative composition includes at least one carboxylated cellulose ester based polyglucose polymer, an alcohol based solvent system, and a cosmetically acceptable additive. The polyglucose polymer is obtained by reacting at least one cellulose ester with a non-aromatic cyclic anhydride and neutralizing the reaction product thereof. The polyglucose polymer is soluble in the alcohol based solvent system.

13 Claims, No Drawings

HAIR FIXATIVES INCLUDING CELLULOSE ESTER BASED POLYGLUCOSE POLYMERS

This application is a national stage filing under 35 U.S.C. § 371 of PCT/EP2014/078228, filed Dec. 17, 2014, which claims priority to U.S. Provisional Patent Application No. 61/919,087 filed Dec. 20, 2013, and European Patent Application No. 14155146.5, filed Feb. 14, 2014, the contents of which are each incorporated herein by reference in their entireties.

FIELD OF THE INVENTION

The invention relates to personal care compositions comprising carboxylated cellulose ester based polyglucose polymers. More specifically, the invention relates to hair fixative compositions comprising carboxylated cellulose ester based polyglucose polymers that are soluble in alcohol based solvent systems.

BACKGROUND OF THE INVENTION

Polymers used in personal care applications, such as hair styling and hair fixing, have conventionally been made using synthetic materials. In order for the polymers to be suitable in such personal care applications, they must be soluble in alcohol based systems, and in the case of aerosol based hair sprays, they must also be compatible with the propellant. Conventional synthetic polymers are generally inexpensive and provide acceptable performance; however, because they are not made from renewable resources, they are not sustainable. In addition, replicating the cost and performance of synthetic polymers is not easy.

For example, WO 99/59532 discloses a hydroxypropyl methyl cellulose acetate phthalate, cellulose acetate phthalate and cellulose acetate trimellitate. However, it has been found that at least cellulose acetate phthalate polymers underperformed when compared to the synthetic polymer under the tradename AMPHOMER® in the same system. In addition, although WO 99/59532 discloses a cellulose acetate butyrate succinate under the trade name CAB SU 160-6 as a comparative example, this polymer was considered outside the scope of the alleged invention of WO 99/59532 because it was not compatible in the alcohol based formulation.

Accordingly, there is a need for personal care polymers made from renewable sources that provide equal to or better performance at comparable costs than their synthetic alternatives and that are soluble in alcohol based systems, such as ethanol based systems and optionally, that are also compatible with propellants, such as dimethyl ether.

SUMMARY OF THE INVENTION

In an aspect, the present invention relates to a hair fixative composition comprising at least one carboxylated cellulose ester based polyglucose polymer; an alcohol based solvent system; and a cosmetically acceptable additive. The polyglucose polymer is obtained by reacting at least one cellulose ester with an anhydride, preferably a non-aromatic cyclic anhydride, and the polyglucose polymer is soluble in the alcohol based solvent system.

In another aspect, the present invention relates to a method of preparing a hair fixative composition comprising reacting at least one cellulose ester with an anhydride, preferably a non-aromatic cyclic anhydride, to form a cellulose ester based polyglucose polymer. In a further step, the method comprises dissolving or suspending the cellulose ester based polyglucose polymer in the alcohol based solvent.

In yet another aspect, the present invention relates to the use of the carboxylated cellulose ester based polyglucose polymer as defined herein as a hair fixative polymer in a hair fixative composition, as well as a method of styling hair, comprising applying the carboxylated cellulose ester based polyglucose polymer as defined herein to hair.

DETAILED DESCRIPTION OF THE INVENTION

As used herein, the recitations of numerical ranges by endpoints include all numbers subsumed within that range (e.g., 1 to 5 includes 1, 1.5, 2, 2.75, 3, 3.80, 4, 5, etc.). In addition, it is to be understood that for embodiments including ranges as described herein, the respective lower endpoints and respective upper endpoints described include combinations of the various lower and upper endpoints. For example, for ranges of 1 to 20 and 5 to 10, respectively, the ranges also include, without limitation, 1 to 10 and 5 to 20.

The hair fixative compositions of the present invention comprise carboxylated cellulose ester based polyglucose polymers that combine the features of having a carboxylated cellulose ester backbone having attached at least one ester group and at least one carboxyl functional group.

It has been found that the carboxylated cellulose ester based polyglucose polymers can provide hair fixative polymers that are not only made from renewable sources but that can also provide equal to or better hair styling performance for example with respect to spray rate, viscosity, stiffness and high humidity curl retention, especially as hair spray polymers, at comparable costs to their synthetic alternatives. The inventive polymers are soluble in an alcohol based solvent system and, optionally, they are also compatible with hair styling propellants. In an embodiment, the carboxylated cellulose ester based polyglucose polymers may be free of aromatic esters. In an embodiment, the carboxylated cellulose ester based polyglucose polymers may also be free of phthalates.

The present invention generally relates to hair fixative compositions including at least one carboxylated cellulose ester based polyglucose polymer having the following structure (I):

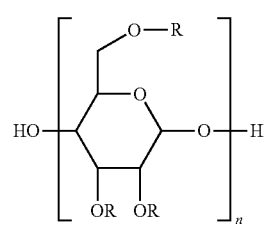

wherein R=H, $R_H$ or $R_A$ or combinations thereof, wherein at least one R is $R_A$ and wherein $R_H$ is: —CO—$R^1$ wherein $R^1$ is $C_1$-$C_{21}$ alkyl group, preferably a $C_1$ to $C_{10}$ alkyl group, and more preferably $C_1$-$C_4$; and $R_A$ is: (a) —CO—$CH_2$—CH($R^2$)—COOH wherein $R^2$=H or $C_1$-$C_{18}$ alkyl or alkenyl group, preferably a $C_6$-$C_{18}$ alkenyl group, and more preferably a $C_8$, $C_{12}$ or $C_{18}$ alkenyl group; b) —CO—CH=CH—COOH; or c) —CO—CH—C(=$CH_2$)—COOH; and wherein n=10-500, more preferably 20-300, and still more preferably 30-100. The hair fixative compositions further include an alcohol based solvent system and a cosmetically acceptable additive, wherein the polyglucose polymer is soluble in the alcohol based solvent system.

In the above formula (I), $R_H$ represents hydrophobic groups and $R_A$ represents groups having acid functionality and, optionally, hydrophobic functionality, In general, the carboxylated cellulose ester based polyglucose polymers are formed by reacting an ester of a polysaccharide, such as cellulose acetate, cellulose propionate, cellulose butyrate, cellulose acetate butyrate and cellulose acetate propionate, with an anhydride, preferably a non-aromatic cyclic anhydride. In an embodiment, the anhydride may be a substituted anhydride or an unsubstituted anhydride. In a further embodiment, the anhydride is more preferably a substituted anhydride. Suitable non-aromatic cyclic anhydrides include, but are not limited to, succinic anhydride or alkenyl succinic anhydride or maleic anhydride or itaconic anhydride, to give a succinate derivative, a maleate derivative or an itaconate derivative or combinations thereof.

Non-limiting examples of carboxylated cellulose ester based polyglucose polymers according to the invention include polymers of formula I wherein $R_H$ is: —CO—$R^1$ wherein $R^1$ is a $C_1$-$C_{21}$ alkyl group, preferably a $C_1$ to $C_{10}$ alkyl group, and more preferably a $C_1$-$C_3$ alkyl group and $R_A$ is: (a) —CO—$CH_2$—CH($R^2$)—COOH wherein $R^2$=H or a $C_1$-$C_{18}$ alkyl or alkenyl group, preferably a $C_6$-$C_{18}$ alkenyl group, and more preferably a $C_8$, $C_{12}$ or $C_{18}$ alkenyl group, and wherein n=10-500, more preferably 20-300, and still more preferably 30-100; or wherein $R_H$ is: —CO—$R^1$ wherein $R^1$ is $C_1$-$C_{21}$ alkyl group, preferably a $C_1$ to $C_{10}$ alkyl group, and more preferably a $C_1$-$C_3$ alkyl group and $R_A$ is: b) —CO—CH=CH—COOH, and wherein n=10-500, more preferably 20-300, and still more preferably 30-100; and wherein $R_H$ is: —CO—$R^1$ wherein $R^1$ is $C_1$-$C_{21}$ alkyl group, preferably a $C_1$ to $C_{10}$ alkyl group, and more preferably $C_1$-$C_3$ and $R_A$ is: c) —CO—CH—C(=$CH_2$)—COOH, and wherein n=10-500, more preferably 20-300, and still more preferably 30-100. In an embodiment, combinations of the above are also included. In an embodiment, the polyglucose polymers suitable for use in the present invention include, but are not limited to, cellulose acetate butyrate (CAB) succinate, CAB octenyl succinate, cellulose acetate propionate (CAP) succinate or combinations thereof.

In an embodiment, the carboxylated cellulose ester based polyglucose polymers of the present invention may be present in the hair fixative composition in an amount from about 1 weight percent to about 10 weight percent, based on the weight of the hair fixative composition. In another embodiment, the polyglucose polymers are present in an amount from about 2 weight percent to about 8 weight percent. In yet another embodiment, the polyglucose polymers are present in an amount from about 3 weight percent to about 6 weight percent.

The polyglucose polymers of the present invention are based on cellulose or cellulose derivatives. Cellulose is a polysaccharide composed of individual anhydroglucose units which are linked through a glycosidic bond. Typically, production of cellulose derivatives involves replacing some of the hydroxyl hydrogen groups of cellulose with a substituent group. The number of substituted hydroxyl groups per anhydroglucose unit is expressed as the degree of substitution (D.S.). As reported in more detail in U.S. Pat. No. 6,841,232, which is incorporated by reference in its entirety herein, D.S. can vary from 0 to 3. In one embodiment, the polyglucose polymers of the invention have a total D.S. of at least 2.

Examples of polyglucose polymers based on cellulose esters suitable for use in the present invention include, but are not limited to cellulose acetate, cellulose acetate butyrate, cellulose acetate propionate, cellulose propionate, cellulose acetate propionate, cellulose propionate, cellulose butyrate and the like. The cellulose esters can be prepared from any cellulose source, including, but not limited to, hardwood pulp, softwood pulp, cotton linters, bacterial cellulose, and regenerated cellulose.

In another aspect, the hair fixative compositions comprise at least one polyglucose polymer and an alcohol based solvent system. As used herein, an alcohol based solvent system comprises at least one alcohol and may include further optional components, such as water, propellant, or other non-alcohol, non-aqueous solvents. The polyglucose polymer must be soluble in the alcohol based solvent system. In an embodiment, the amount of alcohol present in the solvent system may be about 1 weight percent or greater, in another embodiment preferably about 15 weight percent or greater, and in yet another embodiment, more preferably from about 25 weight percent or greater. In an embodiment, the amount of alcohol present in the solvent system may be about 99 weight percent or less, in another embodiment preferably about 50 weight percent or less and in yet another embodiment more preferably about 40 weight percent or less, based on total weight of the solvent system. In another embodiment, the alcohol solvent system may be anhydrous.

In an embodiment of the invention, the hair fixative composition will include no more than about 85% volatile organic compounds (VOC), such as alcohol and/or propellant with the remainder of the solvent being water. In another embodiment, the hair fixative compositions will comprise no more than about 55% volatile organic compounds.

For purposes of the present invention, the term "soluble" means that from about 1 to about 10 weight percent, in another embodiment, preferably from about 3 to about 6 weight percent of the polyglucose polymer is soluble, with or without neutralization, in the alcohol based solvent system. In an embodiment, alcohol based solvent systems suitable for use in the present invention comprise at least one $C_1$-$C_6$ straight or branched chain alcohol or mixtures thereof and, optionally, water, optionally one or more propellants and optionally one or more other non-alcohol, non-aqueous solvents. In an embodiment, the alcohol based solvent system preferably includes at least one $C_2$ or $C_3$ alcohol or mixtures thereof.

In an embodiment of the invention, the hair fixative compositions optionally further include at least one neutralizing agent. In an embodiment of the invention, the polyglucose polymer is generally at least about 70% neutralized. In another embodiment, the polyglucose polymer is at least about 80% neutralized, and in an even further embodiment, the fixative polymer is 100% neutralized. Suitable basic neutralizing agents compatible with the composition can be employed, even inorganic materials such as sodium or potassium hydroxide. Generally organic amines or alkanolamines are readily used for neutralization. In an embodiment, the neutralizing agents include, but are not limited to ammonia; primary, secondary and tertiary amines; alkanolamines; and, hydroxyamines such as 2-amino-2-methyl-propanol and 2-amino-2-methyl-1,3-propanediol, mono-, di- and tri-long chain fatty amines containing a $C_4$ to $C_{24}$ hydrocarbon chain, ethoxylates and propoxylates long chain ($C_4$ to $C_{24}$) fatty amines and mixtures thereof. In another embodiment, the neutralizing agents include aminomethyl-propanol, and di-methyl stearamine, inorganic materials, such as sodium hydroxide and potassium hydroxide, and triethanolamine. In an embodiment of the invention, the neutralizing agent is an organic amine or alkanolamine. In an embodiment, combinations of neutralizing agents may also be used.

In an embodiment, the hair fixative compositions have spray rate in a range from about 0.3 to about 1.5 grams/sec. in an 80% VOC system at 3.5% solids and 40% DME, in another embodiment, preferably from about 0.5 grams/sec. to about 1.2 grams/sec., and in another embodiment, more preferably from 0.75 about to 0.9 grams/sec.

In addition to the above-described solvent systems, the present invention may further optionally include one or more propellants. In an embodiment of the invention where the hair fixative composition is a spray application, the polyglucose polymer is compatible with the propellant. By compatible, it is meant that the polyglucose polymer in the solvent system does not phase separate when the solution is mixed with the propellant. In an embodiment, the polyglucose polymer is preferably compatible with dimethyl ether as the propellant. For purposes of the present invention, the term "compatible" means that up to about 10 weight percent of the polyglucose polymer is soluble in the hair fixative composition that includes the propellant. In another embodiment, the polyglucose polymer is preferably soluble from about 1 to about 10 weight percent, and in yet another embodiment, from about 2 to about 8 weight percent and in still yet another embodiment from about 3 to about 6 weight percent in the hair fixative composition that includes the propellant.

Spray applications of the present invention require a mechanical device or pressurized aerosol container to generate the spray. The devices can be manual such as a pump or squeeze bottle or typical aerosol device such as bag-on-nozzle or pressurized can. If a pressurized can is used then the hair styling formulations of the present invention may further include a propellant. Such propellants include, without limitation, ethers, such as dimethyl ether; one or more lower boiling hydrocarbons such as $C_3$-$C_6$ straight and branched chain hydrocarbons, for example, propane, butane, and isobutane; halogenated hydrocarbons, such as, hydrofluorocarbons, for example, trichlorofluoromethane, dichlorodifluoromethane, 1,1-difluoroethane and 1,1,1,2-tetrafluoroethane, present as a liquefied gas; and the compressed gases, for example, nitrogen, air and carbon dioxide as well as mixtures of these propellants. In an embodiment of the invention, the propellant is present in an amount of about 25% to about 80% by weight of the hair fixative composition including the solvent system. In a further embodiment, the propellant is present in an amount of about 30% to about 60% by weight. Alternatively, in certain spray applications, such as bag-on-nozzle spray applications or pump spray applications, such optional propellants are not required. The hair fixative compositions of the present invention include, but are not limited, to aerosol and non-aerosol hairsprays.

In general, in another aspect of the invention, the method for preparing the hair spray formulations of this invention includes dissolving, suspending or diluting the polyglucose polymer in the selected solvents, adding any modifying agents depending on the desired properties, and thereupon combining the resulting solution with the selected aerosol propellant.

With regard to amounts of the various components, in an embodiment the hair fixative compositions of the present invention may contain the polyglucose polymer in a concentration ranging from about 1 to 10%, by weight; the solvent in a concentration ranging from about 30 to 90%, by weight; and, the propellant concentration in a range from 20 to 75%, by weight. In another embodiment the hair fixative compositions of the present invention may contain the polyglucose polymer in a concentration ranging from about 2 to 8%, by weight; the solvent in a concentration ranging from about 25 to 55%, by weight; and, the propellant concentration in a range from 25 to 55%, by weight.

In yet another aspect, the present invention relates to the use of the carboxylated cellulose ester based polyglucose polymer as defined herein as a hair fixative polymer in a hair fixative composition, as well as a method of styling hair, comprising applying the carboxylated cellulose ester based polyglucose polymer as defined herein to hair. In one embodiment the hair fixative composition is in the form of a spray, in one embodiment the spray is an aerosol spray, in one embodiment the spray is a non-aerosol spray. In one embodiment the hair fixative composition is in the form of a mousse. In one embodiment the hair fixative composition is in the form of a gel.

The application of the hair styling formulations of the present invention may be prior to, during, or after the desired hair style has been achieved.

Optionally, cosmetically acceptable additives may be incorporated into the hair fixative compositions of this invention in order to modify certain properties thereof. One such optional additive may, in additional to the polyglucose polymer, a second polymer, such as a hair fixative polymer. Non-limiting examples of these additional hair fixative polymers include: from Akzo Nobel Surface Chemistry LLC, AMPHOMER® 4961, AMPHOMER®, and AMPHOMER® LV-71 polymers (octylacrylamide/acrylates/butylaminoethyl methacrylate copolymer), AMPHOMER® HC polymer (acrylates/octylacrylamide copolymer) and BALANCE® CR polymers (acrylates copolymer), BALANCE® 47 polymer (octylacrylamide/acrylates/butylaminoethyl methacrylate copolymer), RESYN® 28-2930 polymer (VA/crotonates/vinyl neodecanoate copolymer), RESYN® 28-1310 polymer (VA/Crotonates copolymer), FLEXAN® polymers (sodium polystyrene sulfonate), DynamX polymer (polyurethane-14 (and) AMP-Acrylates copolymer), RESYN® XP polymer (acrylates/octylacrylamide copolymer), STRUCTURE® 2001 (acrylates/steareth-20 itaconate copolymer) and STRUCTURE® 3001 (acrylates/ceteth-20 itaconate copolymer); from Ashland Inc., OMNIREZ-2000® (PVM/MA half ethyl ester copolymer), GANEX P-904® (butylated PVP), GANEX V-216® (PVP/hexadecene copolymer) GANEX® V-220 (PVP/eicosene copolymer), GANEX® WP-660 (tricontanyl PVP), GANTREZ® A425 (butyl ester of PVM/MA copolymer), GANTREZ® AN-119 PVM/MA copolymer, GANTREZ® ES 225 (ethyl ester of PVM/MA copolymer), GANTREZ® ES425 (butyl ester of PVM/MA copolymer), GAFFIX® VC-713 (vinyl caprolactam/PVP/dimethylaminoethyl methacrylate copolymer), GAFQUAT® 755 (polyquaternium-11), GAFQUAT® HS-100 (polyquaternium-28) AQUAFLEX® XL-30 (Polyimide-1), AQUAFLEX® SF-40 (PVP/Vinylcaprolactam/DMAPA Acrylates Copolymer), AQUAFLEX® FX-64 (Isobutylene/Ethylmaleimide/Hydroxyethylmaleimide Copolymer), ALLIANZ® LT-120 (Acrylates/C1-2 Succinates/Hydroxyacrylates Copolymer), STYLEZE® CC-10 (PVP/DMAPA Acrylates Copolymer), STYLEZE® 2000 (VP/Acrylates/Lauryl Methacrylate Copolymer), STYLEZE® W-20 (Polyquaternium-55), Copolymer Series (PVP/Dimethylaminoethylmethacrylate Copolymer), ADVANTAGE® S and ADVANTAGE® LCA (VinylcaprolactamNP/Dimethylaminoethyl Methacrylate Copolymer), ADVANTAGE® PLUS (VA/Butyl Maleate/Isobornyl Acrylate Copolymer); from BASF, The Chemical Company, ULTRAHOLD STRONG (acrylic acid/ethyl acrylate/t-butyl acrylamide), LUVIMER® 100P (t-butyl acrylate/ethyl acrylate/methacrylic acid), LUVIMER® 36D (ethyl acrylate/t-butyl acrylate/methacrylic acid), LUVIQUAT® HM-552 (polyquaternium-16), LUVIQUAT® HOLD (polyquaternium-16), LUVISKOL® K30 (PVP) LUVISKOL® K90 (PVP), LUVISKOL® VA 64 (PVP/VA copolymer) LUVISKOL® VA73W (PVP/VA copolymer), LUVISKOL® VA, LUVISET® PUR (Polyurethane-1), LUVISET® Clear (VP/MethacrylamideNinyl Imidazole Copolymer), LUVIFLEX® SOFT (Acrylates Copolymer), ULTRAHOLD® 8 (Acrylates/Acrylamide Copolymer), LUVISKOL® Plus (Polyvinylcaprolactam), LUVIFLEX® Silk (PEG/PPG-25/25 Dimethicone/Acrylates Copolymer); from The Dow Chemical Company, ACUDYNE® 180, ACUDYNE® 1000, and ACUDYNE® DHR (Acrylates/Hydroxyesters Acrylates Copolymer), ACUDYNE® SCP (Ethylenecarboxyamide/AMPSA/Methacrylates Copolymer), and the ACULYN® rheological modifiers; from Mitsubishi and distributed by Clariant Corporation, DIAFORMER® Z-301, DIAFORMER® Z-SM, and DIAFORMER® Z-400 (methacryloyl ethyl betaine/acrylates copolymer), from Nalco Company, FIXOMER® A-30 and FIXOMER® N-28 (INCI names: methacrylic acid/sodium acrylamidomethyl propane sulfonate copolymer); from The Lubrizol Corporation, FIXATE® G-100 (AMP-Acrylates/Allyl Methacrylate Copolymer), FIXATE PLUS® (Polyacrylates-14), FIXATE® SUPERHOLD (Polyacrylate-2 Crosspolymer), and FIXATE® FREESTYLE (Acrylates Crosspolymer-3) CARBOPOL® Ultrez 10 (Carbomer), CARBOPOL® Ultrez 20 (Acrylates/C10-30 Alkyl Acrylates Copolymer), AVALURE® AC series (Acrylates Copolymer), AVALURE® UR series (Polyurethane-2, Polyurethane-4, PPG-17/IPDI/DMPA Copolymer); polyethylene glycol; water-soluble acrylics; water-soluble polyesters; polyacrylamides; polyamines; polyquaternary amines; styrene maleic anhydride (SMA) resin; polyethylene amine; and other conventional polymer that is polar solvent soluble or that can be made soluble through neutralization with the appropriate base. A combination of one or more of the above hair fixative polymers is also contemplated as within the scope of the present invention. In an embodiment of the invention, the hair fixative polymer is preferably chosen from octylacrylamide/acrylates/butylaminoethyl methacrylate copolymers, acrylates/octylacrylamide copolymers, acrylates copolymer, octylacrylamide/acrylates/butylaminoethyl methacrylate copolymers, VA/crotonates/vinyl neodecanoate copolymers, VA/Crotonates copolymers, sodium polystyrene sulfonates, polyurethane-14 (and) AMP-Acrylates copolymers, acrylates/octylacrylamide copolymers, acrylates/steareth-20 itaconate copolymers, acrylates/ceteth-20 itaconate copolymers and combinations thereof.

In an embodiment of the invention, the optional hair fixative polymer may be present in the hair fixative composition in an amount of about 0.1 to 10% by weight based on total weight of the composition. In a further embodiment, the fixative polymer is present in an amount of about 1 to 10% by weight and in a further embodiment in an amount of about 1 to 7% by weight.

Further optional cosmetically acceptable additives may also include: plasticizers, such as glycols, phthalate esters and glycerine; silicones; emollients, lubricants and penetrants such as lanolin compounds, protein hydrolyzates and other protein derivatives, ethylene oxide adducts, and polyoxyethylene cholesterol; UV absorbers; dyes and other colorants; and, perfumes. Mixtures of these optional additives may also be included. As previously noted, the polymeric binders of this invention show little or no tendency to adversely chemically interact with such additives.

Further optional ingredients can include, but are not limited to, preservatives, colorants, fragrances, viscosity modifiers, vitamins, herbal extracts such as sterols, triterpenes, flavonoids, coumarins, non-glycosidic diterpenes (sterebins) spathulenol, decanoic acid, 8,11,14-ecosatrienoic acid, 2-methyloctadecane, pentacosane, octacosane, stigmasterol, bsitosterol, a- and b-amyrine, lupeol, b-amyrin acetate, and pentacyclic triterpene, include sunscreen actives such as such as a p-methoxycinnamate or an aminobenzoate (UVB absorber) or benzone or an anthranilate (UVA absorber medicaments, moisturizers, anti-itch or anti-dandruff ingredients and the like.

The resulting hair fixative formulations exhibit the characteristics required of such a product. They possess good antistatic properties, adhere well to hair, are easily removed by soapy water or shampoos, allow the hair to be readily recombed, do not yellow on aging, do not become tacky when exposed to high humidities, and have excellent curl retention under high humidity conditions.

The method of preparing the hair fixative compositions of the present invention can be performed in a number of different ways, and depends on the polyglucose polymer used. However, in a further aspect of the invention, the invention provides a non-limiting method for preparing a hair fixative composition. The method comprises suspending or dissolving the polyglucose polymer in an alcohol based solvent systems, for example comprising one or more $C_1$-$C_6$ alcohols. In an embodiment, the method may further include neutralizing the solution with a neutralizing agent, such as aminomethylpropanol. In an embodiment, the one or more alcohols may comprise ethanol in combination with isopropanol or n-propanol, optionally in a weight ratio of about 80:20 to about 20:80 ethanol to isopropanol. In yet another embodiment, optionally, the method further includes the step of adding propellant to the composition. In a further optional step, the method may also include adding water to the composition either before, during, or after suspending the polyglucose polymer in the alcohol or after the neutralizing step.

In an embodiment, the polyglucose polymers of the present invention are suitable for use in hair fixative compositions, such as hair sprays, mousses or gels.

The following examples are intended to exemplify the present invention but are not intended to limit the scope of the invention in any way. The breadth and scope of the invention are to be limited solely by the claims appended hereto.

EXAMPLES

General Synthesis Method for Polyglucose Polymers

A reaction vessel equipped with an agitator and condenser kept under nitrogen atmosphere and immersed in an oil bath for heating was charged with appropriate amounts of cellulose acetate butyrate (CAB) or cellulose acetate propionate (CAP), acetic acid, sodium acetate and succinic anhydride or ocetnyl succinic anhydride (OSA). The mixture was heated to 90-95° C. under stirring until the reaction showed completion as monitored by IR for the disappearance of the anhydride peak. The reaction mixture was then cooled to about 60° C. and cold water (around 5 times the weight of CAB or CAP used) was slowly added to this reaction mixture under vigorous stirring. After stirring for 30 min., the solid separated was filtered, washed with water until all the residual acetic acid was washed off and dried in oven at 45° C. overnight to give solid product.

Samples of the cellulose acetate butyrate (CAB) succinate, octenyl succinate and cellulose acetate propionate (CAP) succinate were prepared using various levels of succinic or octenyl succinic anhydride (ranging from about 15 to about 50 wt % based on weight percent of the CAB or CAP), as shown in Table 1, to determine the impact on the properties of the polymer. Table 2 summarizes the reactions carried out and the polymer properties, including acidity value and solubility parameters. Table 2 also includes data on CAB-SU160 (a CAB succinate sold by the Eastman Chemical Company) as a comparative example.

Determination of Spray Rate
Materials/Equipment:
Vented fume hood
Safety glasses
Top loading balance (0.01 gram accuracy)
Seconds' timer
Procedure: Run in Duplicate
Aerosol Hair Spray
1 Weigh can of hair spray and record weight.
2 Place can in fume hood. Using constant pressure, depress actuator for ten seconds.
3 Re-weigh can and record weight.

Calculation: Initial Weight−Weight After Spraying=grams/second

Note: if duplicates do not agree to within 0.03 g/sec, repeat procedure

Non-Aerosol Hair Spray
1 Weigh pump bottle of hair spray and record weight.
2 Place bottle in fume hood. Consistently and completely, depress the actuator ten times ("bursts").
3 Re-weigh pump bottle and record weight.

Calculation: Initial Weight−Weight After Spraying=grams/"burst"

Note: if duplicates do not agree to within 0.03 g/"burst", repeat procedure

Valve Specification (procured from a company called Aptar)
Product VX-81
Body: VX Barbed 0.013 NOVT ARIAN
Stem: VX80 0.343 FC 1×0.013 ORIFICE
GASKET: VX 0.045 BUTYL CODE 501
SPRING: VS STAINLESS STEEL 0.018 OPEN C
CUP: HIPRO BNA PGFR GSK AL EP T/B D
TUBE: 0.122 ID
TUBE LENGTH: 09 00/16"
Actuator Specification (from Aptar)
REF NO: XL002838
PRODUCT: XL200 SHIP OUT
LABNUM: XL200 VX MISTY TAP 0.023 MISTY
BUTTON: VX XL 200 MISTY TAP WHITE
INSERT: 0.023 MISTY BLACK

TABLE 1

| Example No. | CAB | CAP | Acetic Acid | Sodium Acetate | Succinic Anhydride | OSA |
|---|---|---|---|---|---|---|
| 1 | 30 | — | 45 | 24 | 4.5 | — |
| 2 | 60 | — | 75 | 24 | 12 | — |
| 3 | 60 | — | 75 | 24 | 15 | — |
| 4 | 165 | — | 247.5 | 66 | 49.5 | — |
| 5 | 60 | — | 90 | 24 | 24 | — |
| 6 | 60 | — | 90 | 24 | 27 | — |
| 7 | 60 | — | 60 | 24 | — | 24.7 |
| 8 | 60 | — | 60 | 24 | — | 37.1 |
| 9 | — | 40 | 40 | 8.2 | 9.9 | — |
| 10 | — | 40 | 40 | 10.4 | 12.7 | — |
| 11 | — | 40 | 40 | 13 | 15.5 | — |

* Weights shown are in grams.

TABLE 2

| Example No. | CAB + wt % of SA or OSA used | Acidity. mg KOH/g (meq/g) | Solubility in Ethanol (3.5 wt % polymer) | Solubility in Ethanol after neutralization with AMP (3.5 wt % polymer) | Compatibility in 80% VOC ethanol system + 40% DME | Spray rate g/sec |
|---|---|---|---|---|---|---|
| Comparative Example (CAB-SU160)* | | 60 (1.07) | Insoluble | Not known | Not known | — |
| 1 | CAB-15% SA | 46 (0.82) | Insoluble | Insoluble | Not tested | — |
| 2 | CAB-20% SA | 65 (1.16) | Insoluble | Soluble | Soluble | 0.83 |
| 3 | CAB-25% SA | 86 (1.53) | Soluble | Soluble | Soluble | 0.77 |
| 4 | CAB-30% SA | 106 (1.89) | Soluble | Soluble | Soluble | 0.81 |
| 5 | CAB-40% SA | 109 (1.94) | Soluble | Soluble | Soluble | 0.80 |
| 6 | CAB-45% SA | 121 (2.16) | Insoluble | Soluble | Soluble | 0.79 |
| 7 | CAB-41% OSA | 57 (1.02) | Insoluble | Insoluble | Not tested | — |
| 8 | CAB-62% OSA | 91 (1.63) | Insoluble | Soluble (at 2.6%) | Soluble (at 2.6%) | 0.84 |
| 9 | CAP-25% SA | 83 (1.48) | Insoluble | Soluble | Soluble | 0.79 |

TABLE 2-continued

| Example No. | CAB + wt % of SA or OSA used | Acidity. mg KOH/g (meq/g) | Solubility in Ethanol (3.5 wt % polymer) | Solubility in Ethanol after neutralization with AMP (3.5 wt % polymer) | Compatibility in 80% VOC ethanol system + 40% DME | Spray rate g/sec |
|---|---|---|---|---|---|---|
| 10 | CAP-32% SA | 95 (1.70) | Insoluble | Soluble | Soluble | 0.82 |
| 11 | CAP-39% SA | 104 (1.86) | Insoluble | Soluble | Soluble | 0.86 |

*Kevin Edgar, Polymers Paint Colour Journal, 1993, Vol. 183, page-564;
*Number average molecular weight reported as 20,000 and Degree of Polymerization (DP) reported as 60 (i.e. 60 glucose units)

The CAB and CAP used to make the succinate derivatives identified in Table 2 are available from Eastman Chemical Company under the trade name CAB-553-0.4 and CAP-504-0.2 respectively. Reported data from Eastman on both these raw-materials is given below:

CAB-553.04: DS values—Acetate 0.1 and Butyrate 2.0. MWn=20,000 (number average molecular weight as determined by GPC using polystyrene equivalents)

CAP-504-0.2: DS values—Acetate 0.1 and Propionate 2.1. MWn=15,000 (number average molecular weight as determined by GPC using polystyrene equivalents)

As described in PCT patent publication no. WO 99/59532 to Dupuis, the CAB-SU160 ester cellulose acetate butyrate succinate sold by Eastman Chemical Company that was tested is reported to be insoluble and thus not suitable for use in the present invention.

A. Subjective Test Procedures

Subjective evaluations as provided in the Examples comparing AMPHOMER® polymer, each using 3.5 wt % of the polymers using 80 wt % VOC ethanol-water and 40 wt % DME or as otherwise identified using statistical design method at 95% confidence level were conducted. The results of the Subjective Evaluations conducted are reported in the Tables that follow.

The following procedures were used to conduct the evaluations of the subjective performance of the polyglucose polymers of the present invention.

Gloss:
Gently handle the swatches so as not to break the films. Visually inspect the swatches to determine which has more shine/gloss.

Stiffness:
Gently handle swatches and feel for differences in stiffness. Using two fingers, hold the middle of the swatch in a horizontal position—does one bend more than the other? Choose the one that is more rigid.

Spring:
While holding the swatch in one hand, gently pull on an edge with the other hand three times only. Look for spring back, and bounce. The more elastic the better the Spring.

Webbing:
While holding the swatch in both hands, gently pull outward on the edges approx. 4". (Do this three times only to avoid damage to the bonds. If the bonds are destroyed then the dry combing may appear to be easier to comb). The more net like the better the Webbing.

Dry Comb:
Comb through each swatch (5) times and evaluate ease of combing. Choose the one that combs more easily.

Flake:
Visually inspect both swatches after combing. Check the teeth of the comb for flake accumulation. Holding the swatch at the bound end run your fingernail down the length of the tress then inspect. Choose the one with more flakes.

Anti-Stat:
Holding swatch at bound end comb through vigorously 10 times then evaluate for extent of fly aways generated. Choose the one with more fly aways.

Feel:
Handle swatches and determine preference. Choose the one that feels more silky/cleaner.

Tables 3 and 4—Subjective Evaluation of CAB/CAP Succinate Polymers vs. Amphomer Using 3.5% Polymer Using 80% VOC Ethanol-Water and 40% DME at 95% Confidence Level

TABLE 3

| Example | Gloss | Stiffness | Spring | Webbing | Dry comb | Flake | Antistat | Feel |
|---|---|---|---|---|---|---|---|---|
| 2 | = | − | − | = | = | = | = | = |
| 3 | = | = | = | = | = | − | = | = |
| 4 | = | = | = | = | + | − | = | = |
| 5 | = | = | = | = | = | = | = | = |
| 6 | = | = | = | = | = | = | = | = |

TABLE 4

| Example | Gloss | Stiffness | Spring | Webbing | Dry comb | Flake | Antistat | Feel |
|---|---|---|---|---|---|---|---|---|
| 9 | − | − | − | = | + | − | + | = |
| 10 | = | − | − | = | = | = | = | = |
| 11 | = | = | = | = | = | = | = | = |

= not statistically different;
+ superior;
− inferior at 95% confidence level

Based on the results shown in Tables 3 and 4, all samples were considered to provide adequate subjective performance. Although the least successful in terms of subjective performance was Example 9, as it did not perform as well as AMPHOMER® polymer in four of the eight categories, it outperformed AMPHOMER® polymer in two of the eight categories.

B. Procedure for Determining High Humidity Curl Retention (HHCR)

The following procedures were used to conduct the evaluations of the objective performance of the polyglucose polymers of the present invention as determined by high humidity curl retention. The high humidity curl retention properties of hair styling compositions including polyglucose polymers of the present invention were measured. The tests were each conducted at 72° F. (22° C.) and 90% Relative Humidity over a period of 24 hours. The tests were performed on 10" long×2-gram swatches of European virgin brown hair (9 replicate swatches per sample). Curl retention testing is run in a humidity chamber set at 70° F./90% Relative Humidity for a total of 24 hours. Readings for % Curl Retention are read and recorded at time intervals of 15, 30, 60, 90 min, 2, 3, 4, 5, and 24 hrs. The hair styling compositions were tested according to the following procedures:

1. Wet hair swatch, comb through to remove tangles and squeeze out excess water (run swatch between thumb and index finger).
2. Apply sample to swatch, gently "work into" swatch and comb through.
3. Roll swatch on ½" diameter Teflon mandrel. Carefully remove rolled swatch from mandrel and secure with two hair clips.
4. Place curls on tray and dry in oven overnight.
5. Remove dried curls from oven and let cool to room temperature.
6. Suspend curls, from bound end of swatch, on graduated clear, transparent curl retention boards.
7. Remove clips from curls and gently unwind with glass rod making sure to "break" the curl.
8. Take initial curl length readings before placing boards and curls into environmental chamber (70° F., 90% relative humidity).
9. Record curl lengths at the 15, 30, 60, 90, 2, 3, 4, 5, and hour time intervals.
10. At conclusion of test, remove boards and curls from chamber.
11. Clean used hair swatches.
12. Calculate % Curl Retention and comparison of samples.

The Samples were prepared as follows:

HHCR was run in a constant temperature and humidity chamber. Curls were rolled on a mandrel and allowed to dry overnight. The curls were then sprayed with the polymer solutions (3.5 wt % polymer using 80% VOC ethanol-water and 40% DME) and allowed to dry. Then the curls were hung on a board placed in the oven and the percent of curl loss was tracked over 24 hrs.

The high humidity curl retention properties of hair styling compositions including polyglucose polymers of the present invention according to the Examples as shown in Tables 5 and 6 that follow were measured and compared to the use of AMPHOMER® polymer in the same hair styling composition.

TABLE 5

High Humidity Curl Retention (HHCR) of Examples 2-8 compared to AMPHOMER ® polymer

| Example | 5 hrs | 24 hrs |
|---|---|---|
| 2 | 53% | 49% |
| 3 | 66% | 62% |
| 4 | 73% | 71% |
| 5 | 69% | 66% |
| 6 | 64% | 60% |
| 8 | 1% | 0% |
| Amphomer | 67% | 63% |

* All Examples in Table 5 except Example 8 were conducted using concentrations of the polymer at 3.5 wt %. Example 8 included the polymer at 2.6 wt %.

As shown in Table 5, all Examples with the exception of Examples 2 and 8 provided HHCR comparable or better than AMPHOMER® polymer. Example 2 was marginally less, but still statistically comparable to AMPHOMER® polymer and Example 8 failed to provide sufficient HHCR.

TABLE 6

High Humidity Curl Retention (HHCR) of Examples 9-11 compared to AMPHOMER ® polymer

| Example | 5 hrs | 24 hrs |
|---|---|---|
| 9 | 71% | 67% |
| 10 | No data | No data |
| 11 | 67% | 65% |
| Amphomer | 73% | 70% |

As shown in Table 6, all Examples with the exception of Example 10, for which no data was generated, provided comparable HHCR to AMPHOMER® polymer.

Example 12

Subjective Test Results Using 2.5% CAB-30% SA vs. 3.5% Amphomer at 80% VOC and 40% DME In this Example, a sample of 2.5% CAB-30% SA (Example 4 at a concentration of 2.5 wt % polymer) was prepared and compared to 3.5% AMPHOMER® polymer each at 80% VOC and 40% DME, with the subjective test results shown in Table 7.

TABLE 7

| Sample | Gloss | Stiffness | Spring | Webbing | Dry comb | Flake | Antistat | Feel |
|---|---|---|---|---|---|---|---|---|
| 2.5% Example 4 CAB-30% SA | = | = | = | = | = | = | = | = |

= not statistically different;
+ superior;
− inferior at 95% confidence level

As shown in Table 7, CAB-30% SA (Example 4 with the lower concentration) showed nearly approximately equal performance in all categories of the Subjective tests as compared to 3.5 wt % AMPHOMER® polymer.

Example 13

High Humidity Curl Retention Using 2.5% CAB-30% SA (Example 4) vs. 3.5% Amphomer Using 80% VOC and 40% DME at 90% RH, 70 Deg° F.

The HHCR properties of a hair styling composition including a sample including 2.5% CAB-30% SA (Example 4, but modified to a lower concentration, i.e. 2.5 wt %) were compared to that of 3.5% AMPHOMER® polymer in the same hair styling composition using 80% VOC and 40% DME at 90% RH, 70 deg° F.

TABLE 8

| Sample | 5 hrs | 24 hrs |
| --- | --- | --- |
| 2.5% CAB-30% SA (Example 4) | 69 | 66 |
| 3.5% Amphomer | 68 | 66 |

The results illustrated in Tables 7 and 8 show that CAB-30% SA (Example 4 with 2.5 wt % polymer) outperformed the Comparative Example including CAB-SU 160, which was not soluble in ethanol, and also outperformed AMPHOMER® polymer in this test as well. That is, Example 4 at the lower polymer concentration is soluble in ethanol (unlike the Comparative Example using CAB SU 160) without neutralization (like AMPHOMER® polymer) and shows performance statistically equivalent to AMPHOMER® polymer, but using a lower amount of polymer.

Example 14

Comparative Example of Subjective Test Results Using 3.5% Cellulose Acetate Phthalate vs. 3.5% Amphomer at 80% VOC and 40% DME In this Comparative Example, a sample of 3.5% cellulose acetate phthalate commercially available from Eastman Chemical Company (under Trade name Eastman C-A-P with DS values of 2.17 for Acetate and 0.92 for Phthalate) was tested and compared to 3.5% AMPHOMER® polymer each at 80% VOC and 40% DME. The subjective test results are shown in Table 9.

TABLE 9

| Experimental | Gloss | Stiffness | Spring | Webbing | Dry Comb | Flake | Antistat | Feel |
| --- | --- | --- | --- | --- | --- | --- | --- | --- |
| Example 14 | = | − | = | − | − | − | = | = |

= not statistically different;
+ superior;
− inferior at 95% confidence level.

As shown in Table 9, the cellulose acetate phthalate sample that tested was inferior to the synthetic polymer, AMPHOMER®, in relation to stiffness, webbing, dry comb and flake. The cellulose acetate phthalate sample was determined to be inferior in one half of the categories of subjective test results and statistically equivalent in the remaining categories. Because of the low subjective performance exhibited and the relatively high cost associated with this polymer, this sample was deemed to not warrant further testing.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described herein, the invention is not intended to be limited to the details shown. Rather, various modifications may be made in the details within the range and scope of equivalents of the claims and without departing from the spirit and scope of the invention.

I claim:

1. A hair fixative composition comprising:
   at least one carboxylated cellulose ester based polyglucose polymer obtained by reacting at least one cellulose ester with at least one non-aromatic cyclic anhydride and neutralizing the reaction product thereof;
   an alcohol based solvent system, wherein the alcohol based solvent system comprises at least one $C_1$-$C_6$ straight or branched chain alcohol or mixtures thereof; and
   at least one cosmetically acceptable additive;
   wherein the at least one carboxylated cellulose ester polyglucose polymer is soluble in the alcohol based solvent system.

2. The hair fixative composition of claim 1 wherein the at least one carboxylated cellulose ester based polyglucose polymer has the following structure (I):

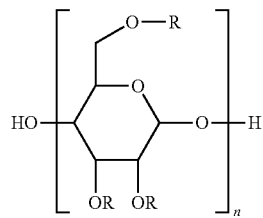

wherein R=H, $R_H$ or $R_A$ or combinations thereof, wherein at least one R is $R_A$ and wherein $R_H$ is: —CO—$R^1$ wherein $R^1$ is $C_1$-$C_{21}$ alkyl group; and $R_A$ is: (a) —CO—$CH_2$—CH($R^2$)—COOH wherein $R^2$=H or a $C_1$-$C_{18}$ alkyl or alkenyl group; or b) —CO—CH=CH—COOH; or c) —CO—CH—C(=$CH_2$)—COOH; and wherein n=10-500.

3. The hair fixative composition of claim 1 wherein the at least one cellulose ester is selected from the group consisting of cellulose acetate, cellulose propionate, cellulose butyrate, cellulose acetate butyrate, cellulose acetate propionate and combinations thereof.

4. The hair fixative composition of claim 1 wherein the at least one non-aromatic cyclic anhydride is a substituted anhydride or an unsubstituted anhydride.

5. The hair fixative composition of claim 1 wherein the at least one non-aromatic cyclic anhydride is selected from the group consisting of a succinic anhydride, alkenyl succinic anhydride, maleic anhydride, itaconic anhydride and combinations thereof.

6. The hair fixative composition of claim 1 wherein the alcohol based solvent system comprises at least one $C_2$ or $C_3$ straight or branched chain alcohol or mixtures thereof.

7. The hair fixative composition of claim 1 wherein the alcohol based solvent system further comprises water, one or more propellants or one or more non-alcohol, non-aqueous solvents or mixtures thereof.

8. The hair fixative composition of claim 1 wherein the at least one carboxylated cellulose ester based polyglucose polymer is present in the hair fixative composition in an amount from 1 weight percent to 10 weight percent, based on the weight of the hair fixative composition.

9. The hair fixative composition of claim 1 wherein the at least one carboxylated cellulose ester based polyglucose polymer is at least 70% neutralized.

10. The hair fixative composition of claim 1 wherein the hair fixative composition is an aerosol hairspray or a non-aerosol hairspray.

11. The hair fixative composition of claim 1 wherein the at least one cosmetically acceptable additive is selected from the group consisting of one or more second hair fixative polymers, plasticizers, UV absorbers, dyes, perfumes, preservatives, viscosity modifiers, vitamins, sunscreen actives, moisturizers, anti-itch or anti-dandruff ingredients and mixtures thereof.

12. A method of preparing a hair fixative composition of claim 1 comprising:
reacting the at least one cellulose ester with the at least one non-aromatic cyclic anhydride to form the at least one cellulose ester based polyglucose polymer;
neutralizing the at least one cellulose ester based polyglucose polymer; and
dissolving or suspending the resulting at least one cellulose ester based polyglucose polymer in the alcohol based solvent system.

13. The method of claim 12 wherein the at least one carboxylated cellulose ester based polyglucose polymer is at least 70% neutralized.

\* \* \* \* \*